US007989566B2

(12) United States Patent
Coughlin et al.

(10) Patent No.: US 7,989,566 B2

(45) Date of Patent: Aug. 2, 2011

(54) PROCESS FOR PRODUCING FLUOROPOLYMERS

(75) Inventors: Michael Cregg Coughlin, Wilmington, DE (US); Ming-Hong Hung, Wilmington, DE (US)

(73) Assignee: DuPont Performance Elastomers LLC, Wilmington, DE (US)

( * ) Notice: Subject to any disclaimer, the term of this patent is extended or adjusted under 35 U.S.C. 154(b) by 86 days.

(21) Appl. No.: 12/354,218

(22) Filed: Jan. 15, 2009

(65) Prior Publication Data

US 2009/0186969 A1 Jul. 23, 2009

Related U.S. Application Data

(60) Provisional application No. 61/011,850, filed on Jan. 22, 2008.

(51) Int. Cl.
*C08F 12/20* (2006.01)

(52) U.S. Cl. ........ 526/193; 526/242; 526/247; 526/249; 526/250; 526/253; 526/254; 526/255; 526/348.8; 562/8; 562/25

(58) Field of Classification Search .................. 526/179, 526/181, 182, 193, 247, 242, 249, 250, 253, 526/254, 255, 348.8; 562/8, 25
See application file for complete search history.

(56) References Cited

U.S. PATENT DOCUMENTS

| | | | |
|---|---|---|---|
| 2,559,749 A | | 7/1951 | Benning |
| 2,559,752 A | | 7/1951 | Berry |
| 2,597,702 A | | 5/1952 | Benning |
| 4,262,101 A | * | 4/1981 | Hartwimmer et al. .......... 526/89 |
| 4,380,618 A | | 4/1983 | Khan et al. |
| 5,738,802 A | * | 4/1998 | Yamamoto et al. ........ 252/62.56 |
| 5,789,508 A | | 8/1998 | Baker et al. |
| 6,395,848 B1 | | 5/2002 | Morgan et al. |
| 2006/0229398 A1 | | 10/2006 | Urban |

FOREIGN PATENT DOCUMENTS

JP 2004-358397 A 12/2004

* cited by examiner

*Primary Examiner* — Mark Eashoo
*Assistant Examiner* — Nicole M Buie-Hatcher

(57) ABSTRACT

An emulsion polymerization process for the production of non-elastomeric fluoropolymers is disclosed wherein at least one fluorosurfactant is employed as dispersant, said fluorosurfactant being a fluoroalkylphosphoric acid ester of the formula X-Rf-$(CH_2)_n$—O—P(O)$(OM)_2$, wherein n is 1 or 2, X═H or F, M=a univalent cation, and Rf is a $C_4$-$C_6$ fluoroalkyl or fluoroalkoxy group. Optionally, a second dispersing agent may be employed in the polymerization, said second agent being a perfluoropolyether having at least one endgroup selected from the group consisting of carboxylic acid, a salt thereof, sulfonic acid and a salt thereof, phosphoric acid and a salt thereof.

6 Claims, No Drawings

PROCESS FOR PRODUCING FLUOROPOLYMERS

CROSS-REFERENCE TO RELATED APPLICATIONS

This application claims the benefit of U.S. Provisional Application No. 61/011,850 filed Jan. 22, 2008.

FIELD OF THE INVENTION

This invention pertains to an emulsion polymerization process for the production of non-elastomeric fluoropolymers wherein at least one dispersing agent is employed, said dispersing agent being a fluoroalkylphosphoric acid ester of the formula X-Rf-$(CH_2)_n$—O—P(O)$(OM)_2$, wherein n is 1 or 2, X═H or F, M=a univalent cation and Rf is a $C_4$-$C_6$ fluoroalkyl or fluoroalkoxy group (branched or non-branched).

BACKGROUND OF THE INVENTION

Production of non-elastomeric fluoropolymers by emulsion and solution polymerization methods is well known in the art; see for example U.S. Pat. Nos. 4,380,618 and 5,789,508. Generally, fluoropolymers are produced in an emulsion polymerization process wherein a water-soluble polymerization initiator and a relatively large amount of dispersing agent (i.e. surfactant) are employed.

Benning (U.S. Pat. Nos. 2,559,749 and 2,597,702) discloses fluorinated aliphatic phosphates that may be employed as emulsifying agents in the aqueous polymerization of unsaturated organic compounds. These phosphate esters are said to be particularly useful in the polymerization of tetrafluoroethylene (TFE) and chlorotrifluoroethylene (CTFE) homopolymers.

Urban (U.S. Patent Application Publication 2006/0229398 A1) discloses the polymerization of fluoromonomers with (meth)acrylates in an aqueous system that employs both 1) a fluoroalkylphosphoric acid ester salt such as phosphoric acid bis(tridecafluorooctyl)ester ammonium salt, and 2) an anionic alkyl sulfonate dispersing agent such as sodium dodecyl sulfate.

Morgan et al. (U.S. Pat. No. 6,395,848 B1) disclose an aqueous dispersion polymerization process utilizing a combination of at least two dispersing agents. At least one dispersing agent is a perfluoropolyether (PFPE) carboxylic acid, sulfonic acid or the salt thereof and at least one dispersing agent is a fluoroalkyl carboxylic acid, sulfonic acid or the salt thereof, or a fluoroalkoxy aryl sulfonic acid or salt thereof.

SUMMARY OF THE INVENTION

One aspect of the present invention provides an emulsion polymerization process for the production of non-elastomeric fluoropolymers wherein the resulting fluoropolymers are readily isolated from the emulsion. This process comprises polymerizing at least one fluoromonomer in an aqueous medium comprising initiator and dispersing agent to obtain an aqueous dispersion of fluoropolymer, wherein said dispersing agent is a fluoroalkylphosphoric acid ester of the formula X-Rf-$(CH_2)_n$—O—P(O)$(OM)_2$, wherein n is 1 or 2, X═H or F, M=a univalent cation, and Rf is a $C_4$-$C_6$ fluoroalkyl or fluoroalkoxy group.

DETAILED DESCRIPTION OF THE INVENTION

The present invention is directed to an emulsion polymerization process for producing a non-elastomeric fluoropolymer. The fluoropolymer may be partially fluorinated or perfluorinated and may be amorphous or crystalline. By "crystalline" is meant that the polymers have some degree of crystallinity and are characterized by a detectable melting point measured according to ASTM D 3418, and a melting endotherm of at least 3 J/g. Melt-processible fluoropolymers that are not crystalline according to the preceding definition are amorphous. Manufacture of amorphous fluoropolymers that are fluoroelastomers, i.e. having a glass transition temperature of less than 20° C., is not included in this invention.

Fluoropolymers made by the process of this invention comprise polymerized units of at least one fluoromonomer. Preferably, fluoropolymers made by the process of this invention comprise copolymerized units of at least one fluoromonomer and a second, different, monomer. Fluoromonomers include, but are not limited to fluorine-containing olefins and fluorine-containing vinyl ethers.

Non-elastomeric fluoropolymer dispersions formed by this invention are comprised of particles of fluoropolymer made from at least one fluorinated monomer, i.e., wherein at least one of the monomers contains fluorine, preferably an olefinic monomer with at least one fluorine or a perfluoroalkyl group attached to a doubly-bonded carbon. The fluoropolymers can be homopolymers of one fluorinated monomer or copolymers of two or more monomers, at least one of which is fluorinated. The fluorinated monomer used in the process of this invention is preferably independently selected from the group consisting of tetrafluoroethylene (TFE), hexafluoropropylene (HFP), chlorotrifluoroethylene (CTFE), trifluoroethylene, hexafluoroisobutylene, perfluoroalkyl ethylenes, fluorovinyl ethers, vinyl fluoride (VF), vinylidene fluoride ($VF_2$), perfluoro-2,2-dimethyl-1,3-dioxole (PDD) and perfluoro-2-methylene-4-methyl-1,3-dioxolane (PMD). A preferred perfluoroalkyl ethylene monomer is perfluorobutyl ethylene (PFBE). Preferred fluorovinyl ethers include perfluoro(alkyl vinyl ether) monomers (PAVE) such as perfluoro(propyl vinyl ether) (PPVE), perfluoro(ethyl vinyl ether) (PEVE), and perfluoro(methyl vinyl ether) (PMVE). Non-fluorinated olefinic comonomers such as ethylene and propylene can be copolymerized with fluorinated monomers.

Fluorovinyl ethers also include those useful for introducing functionality into non-elastomeric fluoropolymers. These include $CF_2$═CF—(O—$CF_2CFR_f)_a$—O—$CF_2CFR'_fSO_2F$, wherein $R_f$ and $R'_f$ are independently selected from F, Cl or a perfluorinated alkyl group having 1 to 10 carbon atoms, a=0, 1 or 2. Polymers of this type are disclosed in U.S. Pat. No. 3,282,875 ($CF_2$═CF—O—$CF_2CF(CF_3)$—O—$CF_2CF_2SO_2F$, perfluoro(3,6-dioxa-4-methyl-7-octenesulfonyl fluoride)), and in U.S. Pat. Nos. 4,358,545 and 4,940,525 ($CF_2$═CF—O—$CF_2CF_2SO_2F$). Another example is $CF_2$═CF—O—$CF_2$—$CF(CF_3)$—O—$CF_2CF_2CO_2CH_3$, methyl ester of perfluoro(4,7-dioxa-5-methyl-8-nonenecarboxylic acid), disclosed in U.S. Pat. No. 4,552,631. Similar fluorovinyl ethers with functionality of nitrile, hydroxyl, cyanate, carbamate, and phosphonic acid are disclosed in U.S. Pat. Nos. 5,637,748; 6,300,445; and 6,177,196.

The invention is especially useful when producing dispersions of melt-processible non-elastomeric fluoropolymers. By melt-processible, it is meant that the polymer can be processed in the molten state (i.e., fabricated from the melt into shaped articles such as films, fibers, and tubes etc. that exhibit sufficient strength and toughness to be useful for their intended purpose). Examples of such melt-processible non-elastomeric fluoropolymers include homopolymers such as polychlorotrifluoroethylene or copolymers of tetrafluoroethylene (TFE) and at least one fluorinated copolymerizable monomer (comonomer) present in the polymer usually in sufficient amount to reduce the melting point of the copolymer substantially below that of TFE homopolymer, polytetrafluoroethylene (PTFE), e.g., to a melting temperature no greater than 315° C.

A melt-processible non-elastomeric TFE copolymer typically incorporates an amount of comonomer into the copolymer in order to provide a copolymer which has a melt flow rate (MFR) of about 1-100 g/10 minutes as measured according to ASTM D-1238 at the temperature which is standard for the specific copolymer. Preferably, the melt viscosity is at least about $10^2$ Pa·s, more preferably, will range from about $10^2$ Pa·s to about $10^6$ Pa·s, most preferably about $10^3$ to about $10^5$ Pa·s measured at 372° C. by the method of ASTM D-1238 modified as described in U.S. Pat. No. 4,380,618. Additional melt-processible fluoropolymers are the copolymers of ethylene (E) or propylene (P) with TFE or CTFE, notably ETFE, ECTFE and PCTFE.

A preferred melt-processible non-elastomeric copolymer that may be manufactured by the process of the present invention comprises at least about 40-99 mol % tetrafluoroethylene units and about 1-60 mol % of at least one other monomer. Preferred comonomers with TFE are perfluoroolefin having 3 to 8 carbon atoms, such as hexafluoropropylene (HFP), and/or perfluoro(alkyl vinyl ether) (PAVE) in which the linear or branched alkyl group contains 1 to 5 carbon atoms. Preferred PAVE monomers are those in which the alkyl group contains 1, 2, 3 or 4 carbon atoms, and the copolymer can be made using several PAVE monomers. Preferred TFE copolymers include FEP (TFE/HFP copolymer), PFA (TFE/PAVE copolymer), TFE/HFP/PAVE wherein PAVE is PEVE and/or PPVE, MFA (TFE/PMVE/PAVE wherein the alkyl group of PAVE has at least two carbon atoms) and THV (TFE/HFP/VF2).

The invention is also useful when producing dispersions of polytetrafluoroethylene (PTFE) including modified PTFE. PTFE and modified PTFE typically have a melt creep viscosity of at least $1\times10^8$ Pa·s and, with such high melt viscosity, the polymer does not flow significantly in the molten state and therefore is not a melt-processible polymer. Polytetrafluoroethylene (PTFE) refers to the polymerized tetrafluoroethylene by itself without any significant comonomer present. Modified PTFE refers to copolymers of TFE with such small concentrations of comonomer that the melting point of the resultant polymer is not substantially reduced below that of PTFE. The concentration of such comonomer is preferably less than 1 weight %, more preferably less than 0.5 weight %. A minimum amount of at least about 0.05 wt % is preferably used to have significant effect. The modified PTFE containing a small amount of comonomer modifier has improved film forming capability during baking (fusing). Suitable comonomers include perfluoroolefin, notably hexafluoropropylene (HFP) or perfluoro(alkyl vinyl ether) (PAVE), where the alkyl group contains 1 to 5 carbon atoms, with perfluoro(ethyl vinyl ether) (PEVE) and perfluoro(propyl vinyl ether) (PPVE) being preferred. Chlorotrifluoroethylene (CTFE), perfluorobutyl ethylene (PFBE), or other monomer that introduces bulky side groups into the molecule may also be used.

Further useful non-elastomeric polymers are film forming polymers of polyvinylidene fluoride (PVDF) and copolymers of vinylidene fluoride as well as polyvinyl fluoride (PVF) and copolymers of vinyl fluoride.

The dispersing agent employed in the emulsion polymerization of this invention is a fluoroalkylphosphoric acid ester of the formula X-Rf-$(CH_2)_n$—O—P(O)$(OM)_2$, wherein n is 1 or 2 (preferably n is 1), X═H or F, M═a univalent cation, preferably H, Na, K, Li or $NH_4$, and Rf is a $C_4$-$C_6$ fluoroalkyl or fluoroalkoxy group. The fluoroalkyl and fluoroalkoxy groups may be branched or non-branched. Preferably the fluoroalkyl and fluoroalkoxy groups are perfluorinated. Each M need not be the same. For example, depending on pH of the aqueous solution containing the dispersing agent, one M may be H while the other M is Na or K.

Specific examples of such dispersing agents include, but are not limited to $CF_3CF_2CF_2OCF(CF_3)CH_2OPO(OM)_2$, H—$(CF_2)_6$—$CH_2$—O—P(O)$(OM)_2$ and F—$(CF_2)_5$—$CH_2$—O—P(O)$(OM)_2$. M═H or $NH_4$ are preferred. $CF_3CF_2CF_2OCF(CF_3)CH_2OPO(OH)_2$ and $CF_3CF_2CF_2OCF(CF_3)CH_2OPO(OH)(ONH_4)$ are especially preferred.

Optionally, a second dispersing agent (in addition to the fluoroalkylphosphoric acid esters described above) may be employed in the polymerization process of the invention. In this aspect of the invention, the second dispersing agent is a perfluoropolyether (PFPE) having at least one endgroup selected from the group consisting of carboxylic acid, carboxylic acid salt, sulfonic acid, sulfonic acid salt, phosphoric acid and phosphoric acid salt. The perfluoropolyether used in this invention can have any chain structure in which oxygen atoms in the backbone of the molecule are separated by saturated fluorocarbon groups having 1-3 carbon atoms. More than one type of fluorocarbon group may be present in the molecule. Representative structures have the repeat unit $$(\text{—}CFCF_3\text{—}CF_2\text{—}O\text{—})_n \quad \text{(XI)}$$

$$(\text{—}CF_2\text{—}CF_2\text{—}CF_2\text{—}O\text{—})_n \quad \text{(XII)}$$

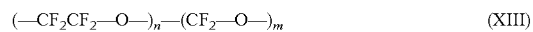

$$(\text{—}CF_2CF_2\text{—}O\text{—})_n\text{—}(CF_2\text{—}O\text{—})_m \quad \text{(XIII)}$$

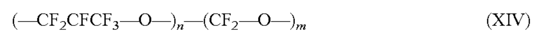

$$(\text{—}CF_2CFCF_3\text{—}O\text{—})_n\text{—}(CF_2\text{—}O\text{—})_m \quad \text{(XIV)}$$

These structures are discussed by Kasai in J. Appl. Polymer Sci. 57, 797 (1995). As disclosed therein, such PFPE can have a carboxylic acid group or salt thereof ("carboxylic group") at one end or at both ends. Such structures are also possible with sulfonic groups or phosphoric groups at one end or at both ends. The "sulfonic" group or "phosphoric" group may be present as the acid or as its ionic salt. In addition, PFPE with acid functionality at both ends may have a carboxylic group at one end and a sulfonic group at the other. The PFPE-sulfonic acids are produced by bubbling $SO_2$ through a solution of the corresponding potassium PFPE carboxylates in dimethylformamide at 140° C. following by extraction and conversion to the acid form by ion exchange. PFPE-phosphoric acids are made by first reducing the PFPE-carboxylic acid or PFPE-acid fluoride to the alcohol and then the alcohol is reacted with either $POCl_3$, followed by hydrolysis in water, or the alcohol is reacted with $P_2O_5$. PFPE having structure XI is available from DuPont. PFPE having structure XII is available from Daikin. PFPE-XIII and XIV are available from Solvay Solexis. The PFPEs useful in the present invention are not limited to the particular PFPEs available from these companies. For monocarboxyl, monosulfonic, or monophosphoric PFPE, the other end of the molecule is usually perfluorinated but may contain a hydrogen or chlorine atom. PFPE having a carboxyl, sulfonic, or phosphoric group at one or both ends that can be used in the present invention have at least 2 ether oxygens, more preferably at least 4 ether oxygens, and even more preferably at least 6 ether oxygens. Preferably, at least one of the fluorocarbon groups separating ether oxygens, and more preferably at least two of such fluorocarbon groups, has 2 or 3 carbon atoms. Even more preferably, at least 50% of the fluorocarbon groups separating ether oxygens has 2 or 3 carbon atoms. Also, preferably, the PFPE has a total of at least 9 carbon atoms, whereby the minimum value of n and n+m in the above repeat unit structures is at least 3. The molecular weight is low enough so that the PFPE is normally liquid at room temperature. While more than one PFPE having a carboxyl, sulfonic, or phosphoric group at one or both ends can be used, normally only one such PFPE is employed.

The amount of total dispersing agent (i.e. amount of fluoroalkylphosphoric acid ester, plus the amount of optional PFPE (if any)) employed in the process of the invention is within typical ranges. Thus, the amount of total dispersing agent can be from about 0.01 wt. % to about 10 wt. %, preferably 0.05-7 wt. %, based on the total weight of water used in the polymerization. The concentration of dispersing agents that may be employed in the polymerization process of the present invention may be above or below the critical micelle concentration (c.m.c.) of each dispersing agent. The c.m.c. is different for different dispersing agents. As one skilled in the art will recognize, the amount of dispersing agent required to achieve a given level of dispersion stability will increase with the amount of polymer to be made at constant particle size. The amount of dispersing agent required for stability also increases with decreasing particle diameter at constant amount of polymer made, since total surface area increases under these conditions. This is observed in some instances for the process of the present invention, which generally yields smaller dispersion particles than a similar process carried out in the absence of PFPE having carboxyl, phosphoric or sulfonic ends. In such instances, if total dispersing agent is not increased, the resultant dispersion can be unstable at room temperature and form a gel. However, the dispersions of this invention are still more stable at room temperature than would be expected from their total dispersing agent level and with their small dispersion particle size. Surprisingly, resultant dispersions that are unstable at room temperature appear to be stable at elevated temperatures used in polymerization, as judged by the small amount of coagulum in the reactor. "Coagulum" is non-water-wettable polymer that can separate from the aqueous dispersion during polymerization. The amount of coagulum formed is an indicator of dispersion stability.

While PFPE having carboxyl, phosphoric or sulfonic ends may be present in major amount in the dispersing agent, such compounds are costly. Of the total dispersing agent, optional PFPE having carboxyl, phosphoric or sulfonic end groups preferably is present in minor amount, i.e., less than half of total dispersing agent by weight. The amount of PFPE having carboxyl, phosphoric or sulfonic ends is more preferably no more than 25 wt. %, most preferably no more than 15 wt. %, based on weight of total dispersing agent. When present, the amount of optional PFPE having carboxyl, phosphoric or sulfonic ends is at least 1 wt. %, preferably at least 3 wt. %, based on the weight of total dispersing agent. The amount of PFPE having carboxyl, phosphoric or sulfonic endgroups that is used will depend on the level of effect (i.e., the particle size) desired. Surprisingly, the use of PFPE having carboxyl, phosphoric or sulfonic ends alone, e.g., in the absence of fluoroalkylphosphoric acid ester dispersing agent, does not yield improved results compared to the use of fluoroalkylphosphoric acid ester dispersing agent alone. That is, the use of a combination of at least two dispersing agents, at least one of the dispersing agents being a fluoroalkylphosphoric acid ester and at least one of the dispersing agents being a perfluoropolyether carboxylic acid, phosphoric acid, or sulfonic acid or salt thereof provides a synergistic effect to the polymerization process, as compared to the use of either type of dispersing agent alone.

As used herein, "combination of dispersing agents" means that the components of the "combination" are present in the reactor during polymerization. The components can be introduced separately, including at different times, and need not be physically combined prior to introduction into the reactor, although they may be so combined. In batch polymerization, all of the dispersing agent may be added to the reactor before polymerization is begun or the addition can be split between a reactor precharge and a later addition, typically after most of the particle nucleation has occurred. The addition of the optional PFPE is preferably with the precharge. In continuous polymerization, dispersing agent components are preferably added as a mixture, typically throughout the polymerization.

The emulsion polymerization process of this invention may be a continuous, semi-batch or batch process. In any process, one or more monomers may optionally be pre-emulsified with surfactant to produce a microemulsion having monomer droplet size less than 10 microns. A high shear mixer is typically employed to form the microemulsion.

In the practice of a preferred embodiment of the invention, the process is carried out as a batch process in a pressured reactor. Suitable vertical or horizontal reactors for carrying out the process of the invention are equipped with stirrers for the aqueous medium to provide sufficient contact of gas phase monomers such as TFE for desirable reaction rates and uniform incorporation of comonomers if employed. The reactor preferably includes a cooling jacket surrounding the reactor so that the reaction temperature may be conveniently controlled by circulation of a controlled temperature heat exchange medium.

In a typical process, the reactor is first charged with deionized and deaerated water as the polymerization medium. The above-described fluoroalkylphosphoric acid ester dispersing agent and optional PFPE having carboxyl, phosphoric or sulfonic endgroups (as described above) are dispersed in the medium. For PTFE homopolymer and modified PTFE, paraffin wax as stabilizer is often added. A suitable procedure for PTFE homopolymer and modified PTFE includes first pressurizing the reactor with TFE. If used, the comonomer such as HFP or perfluoro(alkyl vinyl ether) is then added. A free-radical initiator solution such as ammonium persulfate solution is then added. For PTFE homopolymer and modified PTFE, a second initiator which is a source of succinic acid (e.g. disuccinyl peroxide) may be present in the initiator solution to reduce coagulum. Alternatively, a redox initiator system such as potassium permanganate/oxalic acid is used. The temperature is increased and, once polymerization begins, additional TFE is added to maintain the pressure. The beginning of polymerization is referred to as "kick-off" and is defined as the point at which gaseous monomer feed pressure is observed to drop substantially, for example, about 10 psi (about 70 kPa). Comonomer and/or chain transfer agent can also be added as the polymerization proceeds. For some polymerizations, additional monomers, initiator and/or polymerization agent may be added during the polymerization.

Batch dispersion polymerizations can be described as proceeding in two phases. The initial period of the reaction can be said to be a nucleation phase during which a given number of particles are established. Subsequently, it can be said that a growth phase occurs in which the predominant action is polymerization of monomer on established particles with little or no formation of new particles. The transition from the nucleation to the growth phase of polymerization occurs smoothly. In the polymerization of TFE, this typically occurs over the period when between about 4 and about 10 wt. % polymer solids are present in the reactor.

After batch completion (typically several hours) when the desired amount of polymer or solids content has been achieved, the feeds are stopped, the reactor is vented and purged with nitrogen, and the raw dispersion in the vessel is transferred to a cooling vessel.

The solids content of the dispersion upon completion of polymerization can be varied depending upon the intended use for the dispersion. For example, the process of the invention can be employed to produce a "seed" dispersion with low solids content, e.g., less than 10 wt. %, which is employed as "seed" for a subsequent polymerization process to a higher solids level. In other processes, the solids content of fluoropolymer dispersion produced by the process of the invention is preferably at least about 10 wt. %. More preferably, the fluoropolymer solids content is at least about 20 wt. %. A preferred range for fluoropolymer solids content produced by the process is about 20 wt. % to about 65 wt. %, even more preferably about 20 wt. % to about 55 wt. %, most preferably, about 35 wt. % to about 55 wt. %.

In a preferred process of the invention, polymerizing produces less that about 10 wt. %, more preferably less than 3 wt. %, even more preferably less than 1 wt. %, most preferably less that about 0.5 wt. % undispersed fluoropolymer (coagulum) based on the total weight of fluoropolymer produced.

The as-polymerized dispersion can be stabilized with anionic, cationic, or nonionic surfactant for certain uses. Typically however, the as-polymerized dispersion is transferred to a dispersion concentration operation which produces concentrated dispersions stabilized typically with nonionic surfactants by known methods. Solids content of concentrated dispersion is typically about 35 to about 70 wt. %. Certain grades of PTFE dispersion are made for the production of fine powder. For this use, the dispersion is coagulated, the aqueous medium is removed and the PTFE is dried to produce fine powder.

The dispersion polymerization of melt-processible copolymers is similar except that comonomer in significant quantity is added to the batch initially and/or introduced during polymerization. Chain transfer agents are typically used in significant amounts in order to decrease molecular weight of the copolymers resulting in increased melt flow rate. The same dispersion concentration operation can be used to produce stabilized concentrated dispersions. Alternatively, for melt-processible fluoropolymers that will be employed as molding resins, the dispersion is coagulated and the aqueous medium is removed. The fluoropolymer is dried then processed into a convenient form such as flake, chip or pellet for use in subsequent melt-processing operations.

Water-soluble peroxides which may be used to initiate polymerization in this invention include, for example, the ammonium, sodium or potassium salts of hydrogen persulfate. In a redox-type initiation, a reducing agent such as sodium sulfite, is present in addition to the peroxide. These water-soluble peroxides may be used alone or as a mixture of two or more types. The amount to be used is selected generally in the range of 0.01 to 0.4 parts by weight per 100 parts by weight of polymer, preferably 0.05 to 0.3. During polymerization some of the fluoropolymer polymer chain ends are capped with fragments generated by the decomposition of these peroxides.

Optionally, fluoropolymer gum or crumb may be isolated from the fluoropolymer dispersions produced by the process of this invention by the addition of a coagulating agent to the dispersion. Any coagulating agent known in the art may be used. Preferably, a coagulating agent is chosen which forms a water-soluble salt with the dispersing agent contained in the dispersion. Otherwise, precipitated dispersing agent salt may become entrained in the isolated fluoroelastomer and then retard curing of the fluoroelastomer with bisphenol-type curatives.

Common coagulants include, but are not limited to aluminum salts (e.g. potassium aluminum sulfate), calcium salts (e.g. calcium nitrate), magnesium salts (e.g. magnesium sulfate), or mineral acids (e.g. nitric acid). Salts of calcium, magnesium, or univalent cations with such short chain surfactants are water-soluble, and thus readily removable from the fluoroelastomer.

Instead of employing a coagulant, fluoropolymers produced by this invention may be mechanically or freeze-thaw coagulated.

The fluoropolymers prepared by the process of this invention are useful in many industrial applications including, but not limited to films, seals, wire coatings, tubing and laminates.

EXAMPLES

Test Methods

Comonomer content (PPVE) was measured by FTIR according to the method disclosed in U.S. Pat. No. 4,743,658, col. 5, lines 9-23.

Particle size, i.e., raw dispersion particle size (RDPS) was determined by laser diffraction techniques that measure the particle size distributions (PSD) of materials using a Microtrac Ultrafine Particle Analyzer (UPA). The UPA employs the dynamic light scattering principle for measuring PSD with size range of 0.003 micron to 6.54 micron. Samples were analyzed after collecting the background with water. Measurements were repeated three times and averaged.

The invention is further illustrated by, but is not limited to, the following examples.

Fluoroalkylphosphoric acid esters suitable for use in the emulsion polymerization process of this invention were prepared by the following procedures.

Preparation of 2,2,3,3,4,4,5,5,6,6,7,7-Dodecafluoro-1-Heptanephosphoric Acid Ester [$H(CF_2)_6$—$CH_2O$—$PO(OH)_2$]

In the first step, the phosphorodichloridate was prepared from the fluoroalkyl alcohol. Into a reaction flask equipped with condenser and temperature probe was added 1H,1H,7H-perfluoroheptane-1-ol (150 grams, 0.45 moles) and calcium chloride (10.2 grams, 0.092 moles). While stirring the contents under nitrogen, phosphorus oxychloride (207.3 grams, 1.35 moles) was added to the flask. The temperature of the contents dropped from ambient to about 15° C. The reaction mixture was then heated to 110° C. for 6 hours.

After the reaction was completed (as confirmed by gas chromatography), excess phosphorus oxychloride was distilled off (bp. 105° C.). Further vacuum distillation afforded the desired phosphorodichloridate product as a clear, colorless liquid. Bp. 95° C./0.3 mmHg. Yield=158-170 g.

$^1$H-NMR (400 MHz, acetone-$d_6$): δ 6.83 (tt, J=51 Hz, 5.2 Hz, 1H), 5.20 (m, 2H);

$^{19}$F-NMR (376.89 MHz, acetone-$d_6$): −119.4 (m, 2F), −121.7 (m, 2F), −122.4 (m, 2F), −122.9 (m, 2F), −129.1 (m, 2F), −138.0 (dm, J=51 Hz, 2F).

In a second step, the phosphorodichloridate was hydrolyzed to yield the fluoroalkylphosphoric acid ester. In a round bottomed flask was charged 1H,1H,7H-perfluoroheptane-1-ol, phosphorodichloridate (158 grams, 0.352 moles) prepared above. Water (12.78 grams, 0.71 moles) was added dropwise while the temperature was maintained between 35° and 45° C. (external ice-water cooling). After addition was completed, the reaction mixture was stirred at ambient temperature for 3 hours. The resulting solution was put under high vacuum at 45°-50° C., resulting in a white solid product. Yield was quantitative.

$^1$H-NMR (400 MHz, acetone-$d_6$): δ 9.68 (S, —OH's), 6.82 (tt, J=51 Hz, 10.5 Hz, 1H), 4.61 (m, 2H);

$^{19}$F-NMR (376.89 MHz, acetone-$d_6$): −120.5 (m, 2F), −122.1 (m, 2F), −123.1 (m, 2F), −123.3 (m, 2F), −129.5 (m, 2F), −138.4 (dm, J=51 Hz, 2F).

Preparation of 2,2,3,3,4,4,5,5,6,6,6-Undecafluoro-1-Hexaphosphoric Acid Ester [$F(CF_2)_5$—$CH_2O$—PO $(OH)_2$]

In the first step, the phosphorodichloridate was prepared from the fluoroalkyl alcohol. In a reaction flask equipped with condenser and temperature probe was added 1H,1H-perfluorohexane-1-ol (50 grams, 0.166 moles) and calcium chloride (2.9 grams, 0.026 moles). While stirring the flask contents under nitrogen, phosphorus oxychloride (207 grams, 1.35 moles) was added slowly to the alcohol. The reaction mixture was then heated to 110° C. for 5 hours.

After the reaction was completed, excess phosphorus oxychloride was distilled off. Further vacuum distillation afforded the desired phosphorodichloridate product as a clear, colorless liquid. Bp. 88°-90° C./5 mm Hg. Yield=53.3 g.

$^1$H-NMR (400 MHz, acetone-$d_6$): δ 5.25 (m, 2H);

$^{19}$F-NMR (376.89 MHz, acetone-$d_6$): −80.7 (m, 3F), −119.3 (m, 2F), −122.4 (m, 4F), −125.7 (m, 2F)

In a second step, the phosphorodichloridate was hydrolyzed to yield the fluoroalkylphosphoric acid ester. Into a round bottomed flask was charged 1H,1H-perfluorohexane-1-ol, phosphorodichloridate (83.4 grams, 0.20 moles). Water (7.2 grams, 0.40 moles) was added dropwise while the temperature was maintained between 35° and 45° C. (external ice-water cooling). After addition was completed, the reaction mixture was stirred at ambient temperature for 2 hours. The solution was then put under high vacuum at 60° C. to dry, resulting in a white solid product. Yield was 75.9 grams.

$^1$H-NMR (400 MHz, acetone-$d_6$): δ 4.60 (m, 2H);

$^{19}$F-NMR (376.89 MHz, acetone-$d_6$): −82.2 (m, 3F), −121.5 (m, 2F), −123.9 (m, 2F), −124.0 (m, 2F), −127.3 (m, 2F).

Preparation of 2-Trifluoromethyl-3-oxa-2,4,4,5,5,6,6,6-octafluorohexanoyl Phosphoric Acid Ester [$CF_3CF_2CF_2OCF(CF_3)CH_2OPO(OH)_2$]

In the first step, the fluoroalkyl alcohol was prepared from 2-trifluoromethyl-3-oxa-2,4,4,5,5,6,6,6-octafluorohexanoyl fluoride (HFPO dimer). In a reaction flask equipped with condenser and temperature probe was charged $LiAlH_4$ (13.5 g, 0.355 moles) and 500 ml ether solvent and the contents cooled to 0° C. ($NaBH_4$ may be employed in place of $LiAlH_4$). HFPO-dimer (149.4 g, 0.45 moles) was added slowly and the reaction flask contents temperature was controlled at <10° C. with external cooling. After the addition was completed, the reaction mixture was stirred for 2-3 hours at 5-10° C. The reaction mixture was slowly transferred into a 400 ml 6 N HCl/500 mL ice water mixture and the ether layer was separated. The bottom layer was extracted with 200 mL ether (twice). The ether layers were combined, dried over magnesium sulfate, and then distilled to give the fluoroalcohol 2-trifluoromethyl-3-oxa-2,4,4,5,5,6,6,6-octafluorohexane-1-ol (HFPO dimer alcohol) as a clear, colorless liquid, Bp. 112°-114° C. Yield: 127 grams (89%).

$^1$H-NMR (400 MHz, acetone-$d_6$): δ 4.30 (m);

$^{19}$F-NMR (376.89 MHz, acetone-$d_6$): −80.5 to −82.5 (m, 8F), −129.4 (m, 2F), −134.6 (dm, 1F).

In the second step, the phosphorodichloridate 2-trifluoromethyl-3-oxa-2,4,4,5,5,6,6,6-octafluoro-hexanoyl phosphorodichloridic acid (HFPO dimer phosphoryl chloride) was prepared from the fluoroalkyl alcohol. In a reaction flask equipped with condenser and temperature probe was charged phosphorus oxychloride (255.1 g, 1.662 moles) and calcium chloride (7.14 g, 0.064 moles). While stirring the flask contents under nitrogen, HFPO dimer alcohol (127 g, 0.402 moles) was added in several large portions. The temperature of the contents dropped several degrees. The reaction mixture was heated at 105°-110° C. for 6 hours. The reaction progress was monitored by GC.

After the reaction was completed, excess phosphorus oxychloride was distilled off (Bp. 105° C.). Further vacuum distillation afforded the desired phosphorodichloridate as a clear, colorless liquid. Bp. 35°-38° C./2-3 mm Hg (or 59° C./4.2 mm Hg). Yield was approximately 105 grams (60%).

$^{19}$F-NMR (376.89 MHz, acetone-$d_6$): −80.5 to −82.5 (m, 8F), −129.4 (m, 2F), −135.1 (dm, 1F).

In the third step, the phosphorodichloridate was hydrolyzed to yield the fluoroalkylphosphoric acid ester 2-trifluoromethyl-3-oxa-2,4,4,5,5,6,6,6-octafluorohexanoyl phosphoric acid ester. In a round bottom flask was charged the HFPO dimer phosphoryl chloride prepared above (105 g, 0.242 moles) substrate. Water (9.8 g, 0.544 moles) was added dropwise while the temperature was maintained below 30° C. (external ice-water cooling). After addition was completed, the reaction was stirred at ambient temperature overnight. The 2-trifluoromethyl-3-oxa-2,4,4,5,5,6,6,6-octafluorohexanoyl phosphoric acid ester product was dried in a vacuum oven at 70° C. to give a clear, colorless, viscous liquid. Yield was quantitative.

$^1$H-NMR (400 MHz, acetone-$d_6$): δ 4.80 (m);

$^{19}$F-NMR (376.89 MHz, acetone-$d_6$): −80.6 to −82.5 (m, 8F), −129.4 (m, 2F), −134.7 (dm, 1F).

Example 1

In this example, the dispersing agent employed was 19 wt. % of partially neutralized (i.e. one P—(OH) replaced with P—($ONH_4$))2,2,3,3,4,4,5,5,6,6,7,7-dodecafluoro-1-heptanephosphoric acid ester (DA7) in an aqueous solution, made by the following procedure. To 25 mL of distilled $H_2O$ in a reaction flask, was added a few drops of $NH_4OH$ until pH ~9.0. While the above solution was stirring and being heated at 40° C., several portions (a total of 6.84 g) of 2,2,3,3,4,4,5,5,6,6,7,7-dodecafluoro-1-heptanephosphoric acid ester (prepared as described above) was added. A few drops of $NH_4OH$ was again added to adjust the pH to ~6 in between these portions. The resulting aqueous solution became transparent with some mild foam formation. It had a total volume of 30 mL and 19 wt. % of the partially neutralized dispersing agent (DA7).

Also employed in this example was an initiator solution of 1.0 g ammonium persulfate in 1000 g deionized water.

Deaerated water was used in the polymerizations. It was prepared by pumping deionized water into a large stainless steel vessel and vigorously bubbling nitrogen gas for approximately 30 minutes through the water to remove all oxygen.

The reactor was a 1 liter vertical autoclave made of Inconel®, equipped with a three-bladed ribbon agitator and a baffle insert. No chain transfer agent was used in this example.

A vacuum of approximately 13 PSIG (11.7 kPa) was applied to the reactor. This was used to draw in a solution of 4.8 g of the above solution of dispersing agent and 500 mL deaerated water as a precharge. The reactor was then purged three times (agitator speed=100 revolutions per minute (rpm)) by pressurization with nitrogen gas to 50 PSIG (450 kPa) followed by venting to 1 PSIG (108 kPa) to reduce oxygen content. It was further purged three times (agitator=100 rpm) by pressurization with gaseous tetrafluoroethylene (TFE) to 25 PSIG (274 kPa) followed by venting to 1 PSIG (108 kPa) further insuring that the contents of the autoclave were free of oxygen. The agitator rate was increased to 600 rpm, the reactor was heated to 65° C., and then perfluoro (propyl vinyl ether) (PPVE) (12.8 g) was pumped as a liquid into the reactor.

When at 65° C., the reactor pressure was raised to a nominal 250 PSIG (1.83 MPa) by adding TFE (~38 g). The above prepared initiator solution was fed to the reactor at a rate of 20 mL/min for 1 min. to provide a precharge of 0.02 g ammonium persulfate. It was then pumped at a rate of 0.25 mL/min. until the end of the batch which was defined as the point at which 90 g of TFE had been consumed, measured as mass loss in a TFE weigh tank.

At kickoff (defined as the point at which a 10 PSIG (70 kPa) pressure drop was observed) the polymerization was deemed to have been started, which was also the start point for feeding PPVE at a rate of 0.12 g/min. for the remainder of the polymerization. Reactor pressure was kept constant at 250 PSIG (1.83 MPa) by feeding TFE as needed throughout the entire polymerization.

After 90 g of TFE had been consumed, the agitator was slowed to 200 rpm, all feeds to the reactor were shut off, and the contents were cooled to 30° C. over the course of 30 minutes. The agitator was then turned down to 100 rpm and the reactor was vented to atmospheric pressure. The fluoropolymer dispersion thus produced had a solids content of typically 15-16 wt. %.

Polymer was isolated from the dispersion by freezing, thawing and filtration. The polymer was washed with deionized water and filtered several times before being dried overnight in a vacuum oven at 80° C. and a vacuum of 30 mm Hg (4 kPa). Results are reported in Table 1.

Example 2

The general procedure of Example 1 was repeated except that the solution of dispersing agent contained a combination of 18.3 wt. % dispersing agent DA7 and 3.7 wt. % of a perfluoropolyether (PFPE) having carboxylate endgroups (Krytox® 157 FSL, available from DuPont), prepared by the following procedure. To 25 mL of distilled $H_2O$ in a reaction flask, was added a few drops of $NH_4OH$ until pH ~9.0. While the above solution was stirring and being heated at 40° C., several portions (a total of 6.84 g) of 2,2,3,3,4,4,5,5,6,6,7,7-dodecafluoro-1-heptanephosphoric acid ester (prepared as described above) was added. A few drops of $NH_4OH$ was again added to adjust the pH to ~6 in between these portions. The resulting aqueous solution became transparent with some mild foam formation. It had a total volume of 30 mL. To this solution was then added 1.37 g Krytox® 157 FSL and the solution was heated to 50° C. with stirring. The Krytox® 157 FSL dissolved quickly to give a clear solution.

Example 3

The general procedure of Example 1 was repeated except that the dispersing agent (DA8) employed was 19 wt. % of partially neutralized 2,2,3,3,4,4,5,5,6,6,6-undecafluoro-1-hexaphosphoric acid ester (i.e. one P—(OH) replaced with P—($ONH_4$)) in an aqueous solution, made by the following procedure. To 25 mL of distilled $H_2O$ in a reaction flask, was added a few drops of $NH_4OH$ until pH ~9.0. While the above solution was stirring and being heated at 40° C., several portions (a total of 6.84 g) of 2,2,3,3,4,4,5,5,6,6,6-undecafluoro-1-hexaphosphoric acid ester (as prepared above) was added. A few drops of $NH_4OH$ was again added to adjust the pH to ~6 in between these portions. The resulting aqueous solution became transparent with some mild foam formation. It had a total volume of 30 mL.

Example 4

The general procedure of Example 1 was repeated except that the solution of dispersing agent contained a combination of 18.3 wt. % dispersing agent DA8 and 3.7 wt. % of a perfluoropolyether (PFPE) having carboxylate endgroups (Krytox® 157 FSL, available from DuPont) prepared by the following procedure. To 25 mL of distilled $H_2O$ in a reaction flask, was added a few drops of $NH_4OH$ until pH ~9.0. While the above solution was stirring and being heated at 40° C., several portions (a total of 6.84 g) of 2,2,3,3,4,4,5,5,6,6,6-undecafluoro-1-hexaphosphoric acid ester (as prepared above) was added. A few drops of $NH_4OH$ was again added to adjust the pH to ~6 in between these portions. The resulting aqueous solution became transparent with some mild foam formation. It had a total volume of 30 mL. To this solution was then added 1.37 g Krytox® 157 FSL and the solution was stirred for several hours at room temperature while the Krytox® slowly dissolved, yielding a clear solution.

Example 5

The general procedure of Example 1 was repeated except that the dispersing agent (HFPO-DP) employed was 7.8 g of an 11 wt. % aqueous solution of partially neutralized 2-trifluoromethyl-3-oxa-2,4,4,5,5,6,6,6-octafluorohexanoyl phosphoric acid ester (i.e. one P—(OH) replaced with P—($ONH_4$)) in an aqueous solution. Also monomer feed was discontinued after 60 g of TFE had been consumed.

TABLE I

| Example | Dispersing Agent | Dispersing Agent dry mass (g) | Dispersing Agent mmol | Dispersing Agent ppm | Total Initiator APS (g) | Time to kickoff (min.) | Time to consume 90 g TFE (min.) |
|---|---|---|---|---|---|---|---|
| 1 | DA7 | 0.91 | 2.11 | 1438 | 0.066 | 50 | 60 g in 133 min. |
| 1 | DA7 | 0.91 | 2.11 | 1442 | 0.065 | 48 | 60 g in 131 min. |
| 2 | DA7 + Krytox ® 157 FSL | 0.91 + 0.19 | NA | NA | 0.062 | 34 | 135 |

TABLE I-continued

| | | | | | | | |
|---|---|---|---|---|---|---|---|
| 2 | DA7 + Krytox ® 157 FSL | 0.91 + 0.19 | NA | NA | 0.062 | 35 | 133 |
| 3 | DA8 | 0.84 | 2.11 | 1266 | 0.062 | 28 | 141 |
| 3 | DA8 | 0.84 | 2.11 | 1265 | 0.063 | 25 | 146 |
| 4 | DA8 + Krytox ® 157 FSL | 0.84 + 0.17 | NA | NA | 0.057 | 25 | 124 |
| 4 | DA8 + Krytox ® 157 FSL | 0.84 + 0.17 | NA | NA | 0.058 | 22 | 128 |
| 5 | HFPO-DP | 0.84 | 2.1 | 1350 | 0.048 | 16 | 94[1] |

| Example | % solids | Total batch mass (g) | Total polymer mass (g) | Ave. particle size (nm) | Undispersed polymer (coagulum, g) | Wt. % PPVE |
|---|---|---|---|---|---|---|
| 1 | 11.5 | 632.9 | 72.8 | 136 | 0.5 | 6.6 |
| 1 | 11.4 | 631.2 | 72.0 | 142 | 0.3 | 6.5 |
| 2 | 16.4 | 666.4 | 109.3 | 23 | 0.1 | 8.5 |
| 2 | 16.2 | 666.4 | 108.0 | 22 | 0.6 | — |
| 3 | 16.2 | 663.4 | 107.5 | 154 | 1.0 | 6.1 |
| 3 | 15.5 | 663.9 | 102.9 | 148 | — | 6.5 |
| 4 | 16.4 | 660.7 | 108.4 | 20 | 0.0 | — |
| 4 | 16.4 | 664.5 | 109.0 | 22 | 0.5 | 8.7 |
| 5 | 11.7 | 622.2 | 73 | 114 | 0.8 | 5.5 |

[1]Time to consume 60 g of TFE

What is claimed is:

1. An emulsion polymerization process for the production of a non-elastomeric fluoropolymer, said process comprising polymerizing at least one fluoromonomer in an aqueous medium comprising initiator and at least one dispersing agents to obtain an aqueous dispersion of fluoropolymer, wherein a said dispersing agent is of the formula $CF_3CF_2CF_2OCF(CF_3)CH_2OPO(OM)_2$, wherein M=a univalent cation.

2. The process of claim 1 wherein said dispersing agent is selected from the group consisting of $CF_3CF_2CF_2OCF(CF_3)CH_2OPO(OH)_2$ and $CF_3CF_2CF_2OCF(CF_3)CH_2OPO(OH)(ONH_4)$.

3. The process of claim 1 wherein said at least one fluoromonomer is selected from the group consisting of tetrafluoroethylene, hexafluoropropylene, chlorotrifluoroethylene, trifluoroethylene, hexafluoroisobutylene, perfluoroalkyl ethylene, fluorovinyl ethers, vinyl fluoride, vinylidene fluoride, perfluoro-2,2-dimethyl-1,3-dioxole and perfluoro-2-methylene-4 methyl-1,3-dioxolane.

4. The process of claim 1 wherein said fluoropolymer is selected from the group consisting of polytetrafluoroethylene, polychlorotrifluoroethylene and polyvinylidene fluoride.

5. The process of claim 1 wherein said fluoropolymer comprises copolymerized units selected from the group consisting of i) tetrafluoroethylene and hexafluoropropylene, ii) tetrafluoroethylene and perfluoro(propyl vinyl ether), iii) tetrafluoroethylene, hexafluoropropylene and vinylidene fluoride, iv) ethylene and tetrafluoroethylene, v) ethylene and chlorotrifluoroethylene, and vi) propylene and chlorotrifluoroethylene.

6. An emulsion polymerization process of claim 1 further comprising the introduction of a second dispersing agent, said second dispersing agent being a perfluoropolyether having at least one endgroup selected from the group consisting of carboxylic acid, carboxylic acid salt, sulfonic acid, sulfonic acid salt, phosphoric acid and phosphoric acid salt.

* * * * *